United States Patent [19]

Barringer et al.

[11] Patent Number: 4,788,046

[45] Date of Patent: Nov. 29, 1988

[54] METHOD FOR PRODUCING MATERIALS FOR CO-SINTERING

[75] Inventors: Eric A. Barringer, Waltham; Sheldon I. Lieberman, Burlington; Mark S. Schmidt, West Newton; James D. Hodge, Medway, all of Mass.

[73] Assignee: Ceramics Process Systems Corporation, Cambridge, Mass.

[21] Appl. No.: 85,078

[22] Filed: Aug. 13, 1987

[51] Int. Cl.$^4$ .................. C03C 3/064; C03C 3/020
[52] U.S. Cl. .................. 423/122; 423/158; 423/270; 423/338; 501/12; 501/21; 501/32; 501/17; 501/77; 252/313.1; 252/313.2; 252/315.01; 252/315.6; 252/315.7; 264/60
[58] Field of Search .................. 501/12, 32, 21, 77, 501/17, ; 423/270, 338; 252/313.1, 313.2, 315.01, 315.6, 315.7; 264/60; 163/122, 158

[56] References Cited

U.S. PATENT DOCUMENTS

| | | |
|---|---|---|
| 3,759,683 | 9/1973 | Dislich et al. .................. 501/12 |
| 3,978,248 | 8/1976 | Usami . |
| 4,133,690 | 1/1979 | Muller .................. 501/12 |
| 4,221,047 | 9/1980 | Narken et al. . |
| 4,234,367 | 11/1980 | Herron et al. . |
| 4,336,088 | 6/1982 | Hetherington et al. . |
| 4,413,061 | 11/1983 | Kumar et al. . |
| 4,504,339 | 3/1985 | Kamehara et al. . |
| 4,536,435 | 8/1985 | Utsumi et al. . |
| 4,547,625 | 10/1985 | Tokasi et al. . |
| 4,593,006 | 6/1986 | Takabatake et al. .................. 501/77 |
| 4,624,934 | 11/1986 | Kobuku et al. .................. 501/32 |
| 4,695,403 | 9/1987 | Nishimura et al. . |

OTHER PUBLICATIONS

Shimada et al.-IEEE Trans. on CHMT vol. CHMT6-No. 4 Dec. 1983-pp. 382-388.
Debely et al.-J. Am. Ceram. Soc. vol. 68 (3) C-76-C-78 (1985).
Nishigaki et al.-International Society for Hybrid Microelectronics 1986-pp. 429-437.
Mandai et al.-IMC 1986 Proceedings-pp. 61-64.
Nishimura et al.-IMC 1986 Proceedings-pp. 249-254.

*Primary Examiner*—William R. Dixon, Jr.
*Assistant Examiner*—David M. Brunsman

[57] ABSTRACT

This invention relates to glass-ceramic packages for integrated circuits containing multi-layer, interconnected thick film wiring patterns obtained by co-sintering a glass-ceramic composite and copper, silver, palladium or gold based conductors at temperatures not exceeding about 1000° C. The dielectric systems disclosed herein contains composites of borosilicate glasses and crystalline fillers which are fabricated by either mixing glass frit and the filler or by a sol-gel coating process.

22 Claims, No Drawings

METHOD FOR PRODUCING MATERIALS FOR CO-SINTERING

BACKGROUND

1. Field of Invention

This invention relates to glass-ceramic composite packages for integrated circuits in general, and in particular to glass-ceramic composite materials used in the fabrication of packages. The multi-layer, interconnected thick-film wiring patterns of the packages are obtained by co-firing a glass-ceramic composite and copper, silver, or gold based conductors at temperatures not exceeding about 1000° C.

2. Description of Prior Art

Multi-layer ceramic substrates for mounting integrated circuit chips generally comprise alternating layers of metallic circuits and ceramic insulating layers to form three dimensional interconnect circuits. The substrates are produced either by a thick film printing method or a green sheet lamination method.

The thick film printing method has been used to fabricate hybrid circuits and multi-layer printed interconnect boards. In this process, metal powders and ceramic powders are formulated into metal and dielectric (insulator) inks and then alternately screen printed onto a fired ceramic base. Generally two or three printings of dielectric material are required for every insulating layer and the circuit must be fired after each printing process. Thus, this method is very time consuming because of the large number of printing and firing steps required. The method is also prone to low production yields and is limited in the density of interconnect circuitry. Ceramic layer hermeticity is a major problem affecting yields and is a direct result of using screen printing methods to form insulating layers.

According to the green sheet lamination method, green ceramic sheets on which metal circuits have been printed are successively laminated and then co-fired to form a monolithic interconnect structure (package). Generally, the ceramic green tape is fabricated by the doctor blade casting process from a slurry containing a mixture of ceramic powders, thermoplastic resin, solvents, and other additives (dispersants, plasticizer). Polyvinyl butyral (PVB) is the most commonly used resin system for tape formation. The green tape is blanked into sheets and registration holes are punched. Via holes, which in the final package serve as vertical interconnects between layers, are punched using fixed tooling or a numerically controlled punch press. The via holes are filled and circuit trace patterns are printed using the desired metallization compositions. The individual sheets are then stacked in the proper sequence and laminated to form a solid, composite laminate. The laminate is fired to decompose and remove the organic binder and to sinter the ceramic and metal particles, thus forming a dense body containing the desired three-dimensional wiring pattern.

Aluminum oxide, because of its excellent electrical (insulating), thermal, and mechanical (especially strength) properties has been the ceramic of choice for such substrates. These ceramic bodies, generally containing 4–10 weight percent glass, require sintering temperatures above 1500° C., which thus necessitates the use of refractory metals such as molybdenum or tungsten for the wiring. These metals have poor electrical conductivity as compared to highly conductive metals such as copper, and secondly, they require the use of strongly reducing atmospheres during co-firing necessitating, expensive furnace systems.

Alumina has been an adequate dielectric material for microelectronic packaging in the past; however, the advent of higher frequency and higher speed devices has made clear the deficiencies of the current materials systems. $Al_2O_3$ has a relatively high dielectric constant of about 9.9, causing high signal propagation delay and low signal-to-noise ratio (crosstalk). Furthermore, alumina has a thermal expansion of $6.7 \times 10^{-6}/°C$. (20°–200° C. range) as compared to $3.0-3.5 \times 10^{-6}/°C$. for silicon, which represents significant mismatch in thermal expansion and results in design constraints and reliability concerns (e.g., flip chip technology). Furthermore, the binders used to fabricate green tape do not decompose cleanly during firing at low temperatures (200°–600° C.) in the reducing atmospheres utilized; significant graphitic carbon is generated which requires a high temperature burnout treatment (1100°–1200° C.) prior to raising the temperature to the peak firing condition.

Accordingly, there exists a need for a materials system which allows co-sintering of the ceramic with a conductive metal such as copper, gold, or silver. An IC package fabricated from this system would have significantly improved signal transmission characteristics. To this end, a glass-ceramic material sinterable to a high density at temperatures less than 1000° C. is desirable.

There have been numerous attempts to make such a low temperature co-firable substrate; see for example: Utsume, et al., U.S. Pat. Nos. 4,536,435; Takabatake, et al., 4,593,006; Herron, et al., 4,234,367; Kamehara, et al., 4,504,339; Eustice, et al. (IEEE 36th ECC Proceedings, 1986, pp. 37–47); Nishigaki, et al. Proceedings of the 1985 International Symposium on Microelectronics (ISHM), pp 225–234. Although some similarities exist between this art and the present invention, critical differences and improvements are realized in the present invention. With the exception of Herron, et al., who utilize a cordierite glass-ceramic, the above generally use $Al_2O_3$-glass composites fabricated by mixing $Al_2O_3$ powder and glass frit. These composites generally have dielectric constants between 7.0 and 8.0, higher than what would be desirable in an advanced electronic package.

DISCLOSURE OF THE INVENTION

We have succeeded in making glass-ceramic composites suitable for use as ceramic substrates which have a sintering temperature of approximately 1000° C. or less. Thus, these composites may be co-sintered with copper or other highly conductive metals having relatively low melting points. These composites comprise a variety of crystalline ceramic fillers and a borosilicate glass and are fabricated by either mixing the filler powders with a glass frit or by a sol-gel coating process of the filler. By varying the composition of the composite, one can select sets of properties, primarily fracture strength, dielectric constant, and thermal expansion coefficient, for the desired application.

The present invention employs $Al_2O_3$ and additional ceramic fillers, such as cordierite and quartz, to yield low dielectric constants. These composites are fabricated using either the mixed powder method (ceramic filler plus glass frit) or a sol-gel coated filler method, where the glass coated filler powder is processed as a single powder type rather than mixing two separate powders. This provides additional control of the tape fabrication process and a more homogeneous product. Additionally, glass compositions not possible as single phase glasses from the melt can be utilized through the sol-gel coating approach. Another important feature of the glass-ceramic dielectric is fracture strength; to allow reliable coexistence of the ceramic and the metallurgy a high strength (approximately $\geq 30,000$ psi) is desirable. The glass-ceramics materials from the above listed examples generally exhibit fracture strengths below 30,000 psi, whereas the present invention provides composites having strengths up to about 45,000 psi.

By adjusting the ratio of the glass and frit, it is possible to adjust the thermal expansion coefficient to approximate that of silicon, gallium arsenide or other desired metals which one might use to complete the integrated circuit. Typically, the thermal expansion coefficient will range from approximately $0.5-6 \times 10^{-6}/°C$.

DESCRIPTION OF THE SPECIFIC EMBODIMENTS

The low firing temperature materials of the present invention are glass-ceramic composites comprising a borosilicate glass and a ceramic filler. The glassy material mixed with or used to coat the filler particles is generally a composition based on calcium oxide (CaO), magnesium oxide (MgO), boron oxide ($B_2O_3$), and silicon dioxide ($SiO_2$) or combinations of these materials. Aluminum oxide ($Al_2O_3$) and other oxide additions to the glass can be made to alter the properties of the glass and subsequent composites.

The preferred glass compositions are in the range of approximately 20–57% alkaline earth oxides (MO), 23–40% $SiO_2$, 20–35% $B_2O_3$, and 0–10% $Al_2O_3$. (All compositions herein, except where otherwise stated, are expressed as a weight percent.) The preferred compositions for fritted glass (powder) prepared from essentially single phase glass melts are 25–57% MO, 23–35% $SiO_2$, 25–35% $B_2O_3$, and 0–10% $Al_2O_3$, where in both cases the preferred percentage of alkaline earth oxide (MO) present as MgO is 0–50% and the balance thereof is CaO. For fritted glass materials, reducing the MO or $B_2O_3$ levels below the above values or increasing the MgO ratio much above 50% leads to two-phase, and sometimes devitrified, glasses which may also be difficult to batch and melt. Glasses which have phase separated, but not devitrified, have been successfully employed, yet they are not generally preferred.

The sol-gel coated composite powders are fabricated by mixing suspension of the filler particles (in the preferred embodiments either $Al_2O_3$, spinel, cordierite, mullite, quartz, or mixtures thereof) with a solution of glassy reagent and then adding a precipitating agent. Other filler particles which may be of interest include, but are not limited to: silicates, silica, forsterite, or mixtures and combinations of any of the aforementioned fillers. The precipitating agent causes the glassy component to coat the filler particles. The composite powder is then separated from the solution, dried, calcined and milled. Milling is required to break up the loosely aggregated product into a fine, single-particle population; the powder is then ready for further processing into green tape.

In a preferred embodiment, a slurry is formed by dispersing a filler powder with the aid of a dispersing agent, such as gamma- methacryloxypropyl silane, in dry isopropyl alcohol, although methanol or ethanol are equally applicable. Other preferred dispersants include, but are not limited to, ethylene diamine, triethanolamine (TEOA), and triethylamine (TEA), and ammonium hydroxide. Proper deagglomeration (dispersion) of the powder may be achieved by ball-milling or other milling or mixing processes.

A separate solution of tetraethylorthosilicate (TEOS), a borate such as butyl borate, or boric acid, and soluble calcium and/or magnesium salts, preferably nitrates, in alcohol is prepared. This solution is then added to the slurry and mixed by stirring to form a homogeneous solution. A precipitating agent such as an aqueous solution of ammonium hydroxide is added to the slurry to cause precipitation of the glass forming components; ammonium carbonate may also be present as a co-precipitating agent to aid in complete precipitation of the Ca and Mg cations. The resulting composite is separated from the solution by spray-drying or by centrifugation followed by drying at less than about 200° C. The aggregate powder is calcined and then milled to the appropriate average size. Limited milling is also possible prior to calcining, but this step adds cost and if prolonged may cause degradation of the coating.

Although the preferred coating process described uses an alcohol system, this method could be used with other solvents, precipitating agents, or precursors. For example, this process could also be accomplished using aqueous solutions of silicic acid or boric acid, and calcium and magnesium salts dissolved in water and then precipitated to a sol-gel glass using the appropriate agents.

In a preferred embodiment, the sol-gel coating is uniformly distributed in the product and attached to the filler powder particles such that after drying, calcining, and milling there is a minimal amount of unattached silicate particles in the composite powder, because a single population of coated particles is easier to fabricate with control into a homogeneous product. In a further embodiment, the dried powder is calcined at a temperature preferably between 650° and 800° C. The lower temperature limit is defined by the requirement that the surface area of the dried powder be reduced from approximately $>50$ m$^2$/g to a level of about 1 to 15 m$^2$/g and that the organics burn out so that the carbon level is approximately less than 200 ppm. Too high a calcining temperature causes substantial sintering, thus making milling difficult. In addition, reactions, such as $Al_2O_3$ and glass to form anorthite, become significant above about 800° C.; if this occurs during calcination the resultant powder is often not sinterable below 1000° C.

The sol-gel coating method has several advantages over the mixed filler and frit method. The glass composition can be easily altered by changing precursor concentrations and the product is more homogeneous. Compositions which either are very difficult to melt or which phase separate during cooling, and hence may not be as suitable in frit form, can be easily fabricated using the sol-gel method. For example, a glass comprising 40% $SiO_2$, 30% $B_2O_3$, 22.5% CaO and 7.5% MgO cannot be fully melted at 1550° C., whereas the composition is easily produced by the sol-gel method and is sinterable with a cordierite filler. Finally, as discussed subsequently, sinterable alumina-based composites are possible with 25% glass using the coating method, whereas 40% glass is required to achieve similar sinterability for the same glass composition using the frit method.

The filler material of the composite is generally a crystalline ceramic, including alumina, spinel, or almost any silicate-based oxide material, including cordierite, mullite, forsterite, spodumene, eucryptite, quartz, or any combination of the foregoing. The filler material and the appropriate glass can be chosen to optimize a desired characteristic. For example, in one embodiment an alumina filler might be chosen because of the strength imparted to the fired product. In a further embodiment, alpha-cordierite yields composites with a lower thermal expansion coefficients, which more closely matches that for silicon, and lower dielectric constants (about 5.5). In yet another preferred embodiment, crystalline quartz yields composites with a higher thermal expansion coefficient and a very low dielectric constant of 4.5 to 5.5, depending on the glass used. Additionally, although not a crystalline ceramic filler, fused $SiO_2$ has been successfully employed; during firing the $SiO_2$ reacts with the glass to form a crystalline (primarily cristobalite) $SiO_2$-glass composite.

In a preferred embodiment where reproducibility is important, the particles have a narrow size distribution. As used herein, the term "narrow size distribution" refers to particles whose size range has standard deviation not greater than approximately 50% of the mean. However, the invention is equally applicable to particles with conventional size distributions. Preferably the mean particle size is between 0.5 and 5 micrometers, and it is further preferred that the particles be between 1–3 micrometers in diameter, or less. However, it should be noted that the invention is not limited to any particular size particle, and will be applicable to virtually any size particle desired.

The preferred range of constituent ratios for the starting powders are 40–75% filler using the sol-gel coating method and 40–60% filler for the mixed powder method. The upper limit in filler content was established by sinterability requirements for temperatures less than approximately 1000° C. The upper limit of 60% filler for the mixed powder method is similar to previously disclosed values, yet similar densities are achieved with as much as 15% more filler using sol-gel coated fillers; composites 1 and 2 from Table 2 in Example 3 are illustrative of this point. The lower limit of 40% filler was established because of significant degradation in firing behavior and of key properties below this level, especially for the alumina-based glass-ceramics. Fracture strengths as high as 45,000 psi were achieved for 60% filler, whereas the strength rapidly decreased toward that for bulk glass (about 20,000 psi) as the $Al_2O_3$ level was decreased below 40% ($Al_2O_3$ only filler present). In addition, sticking of composite to the setter during firing becomes a significant problem at high glass content.

The high fracture strength observed herein, especially for the alumina-based composites, is due to two factors. The most important factor, which is specific to the $Al_2O_3$ filler, is the dissolution of a small amount of $Al_2O_3$ into the glass during firing (T≧800° C.), which reacts with the glass to form anorthite (CaO-$Al_2O_3$-2 $SiO_2$). An added benefit of this reaction is that the fired $Al_2O_3$-based composites may be heated in further processing (brazing) to temperatures near the peak firing temperature without causing warpage of the body. A second factor influencing fracture strengths, and in fact leading to more uniform properties in general, is the more uniform fired microstructures resulting from the powder technology disclosed herein.

It is preferred that the filler not react excessively with the glass, because this results in uncontrolled shrinkage and excessive warpage during firing and also generally leads to degraded properites, particularly fracture strength. To moderate effects of any reactions, the filler or glass may be altered. In one preferred embodiment, a mixture of fillers, one reactive and the second relatively inert, may be combined to yield more desired net properties than the two separately. For example, $Al_2O_3$ at 60% mixed with glass A (from Table 1 in Example 2) yields high fracture strengths and dielectric constants of about 7.9, while forsterite (50%) mixed with glass A reacts without densification during firing up to 1000° C. However, a combination of the three constituents (for example, composite #3 from Table 2 in Example 3) densifies acceptably and yields high fracture strength and reduced dielectric constant.

Detrimental reactions may also be overcome by a change in the glass composition. For example, cordierite combined with glass A dissolves slowly during firing at 850° C. and rapidly above about 900° to form additional glass and a small amount of an unidentified crystalline phase. However, addition of MgO to the glass (for example, glasses C through H and J-L in Table 1 in Example 2) allows the cordierite-based composites to be fired at temperatures as high as about 950° C. with minimal cordierite dissolution, thereby yielding improved mechanical and dielectric properties. Furthermore, small additions of $Al_2O_3$ as a co-filler results in improved fracture strength due to the reaction with the glass and anorthite formation. A preferred embodiment of the present invention is the combination of cordierite, $Al_2O_3$ and a magnesium calcium borosilicate (CMBS) glass to yield good net properties, particularly fracture strength (30,000–40,000 psi), dielectric constant (about 5.5–6.5) and thermal expansion coefficient (approximately $3-4\times10^{-6}/°C$.) Another preferred embodiment of the present invention is the combination of quartz and glass with $Al_2O_3$ and/or cordierite to yield comparable properties.

Another preferred embodiment of the invention is the use of MgO additions to the glass phase of the final composite, either in the form of a reactive filler, such as forsterite or cordierite added to a calcium borosilicate (CBS) glass, or as a CMBS glass, to impart chemical stability to the fired composites. Although Takabatake, et al. disclose the addition of $Al_2O_3$ to their glass to impart chemical stability, $Al_2O_3$ was not successful in the present case. During firing of Composite 1, $Al_2O_3$ and a CBS glass, some $Al_2O_3$ dissolves into the glass, but is subsequently consumed in forming anorthite, thereby leaving a residual borosilicate glass phase that is soluble in water. Hence the composite fails a water leaching test (2 hours in boiling water) for which ≦1% weight loss is required. However, the addition of MgO to the composites significantly improves chemical stability; when anorthite forms during firing the MgO remains in the residual glass phase, thereby imparting stability.

The invention may be more readily understood by reference to the following examples.

EXAMPLE 1

62.98 g of tetraethyl silicate was reacted with 10.84 g acidified water in 1800 g isopropanol to form a silanol. The silanol was reacted with 24.94 g of tri-butyl borate. In this solution 96.76 g of $Ca(NO_3)_2\cdot4H_2O$ was dissolved. A second solution containing 140 g of $Al_2O_3$ (particle size range of approximately 0.5–0.8 micrometers) was prepared as a slurry, using gamma-methacryloxypropyl silane as a dispersant. The two solutions were mixed. After stirring for ½ hour, an addition of 600 g of 50 volume percent solution of ammonium hydroxide containing approximately 100 g ammonium carbonate was made, resulting in precipitation of the precursors. The solution was then centrifuged and the supernatant discarded. The resulting powder cake was dried and calcined.

Silicic and boric acids in aqueous solutions have been substituted into the above procedure for tetraethylorthosilicate and tri-butyl borate, respectively. Also, magnesium salts may be used in addition to or in lieu of calcium salts.

EXAMPLE 1A

The following were dissolved in 250 g methanol: 105.41 g TEOS, 44.05 g B(OH)$_3$, 77.47 g Ca(NO$_3$)$_2$·4H$_2$O, 40.76 g Mg(NO$_3$)$_2$·6H$_2$O and stirred for one hour. A second solution containing 120.0 g cordierite slurried in 1200 ml IPA with 4 ml NH$_4$OH was stirred for one hour. The first solution was added to the second, and the resultant solution was stirred for one-half hour. To this, 500 ml of a 50 volume percent aqueous solution of NH$_4$OH was added for precipitation. After centrifuging, the solid was dried and calcined to 750° for one hour.

EXAMPLE 2

The following glasses were made:

| Glass | SiO$_2$ | B$_2$O$_3$ | MgO | CaO | Al$_2$O$_3$ | Phases |
|---|---|---|---|---|---|---|
| A | 30.5% | 31.5% | | 38.0% | | 1 |
| B | 30.5 | 31.5 | 38.0 | | | 1 |
| C | 31.2 | 31.8 | 15.5 | 21.5 | | 1 |
| D | 29.5 | 30.2 | 13.0 | 18.2 | 9.1 | 1 |
| E | 33.0 | 31.0 | 6.75 | 20.25 | 9.0 | 1 |
| F | 33.0 | 31.0 | 11.2 | 15.8 | 9.0 | 1 |
| G | 36.0 | 27.0 | 6.75 | 20.25 | 10.0 | 2 |
| H | 36.0 | 27.0 | 13.5 | 13.5 | 10.0 | 2 |
| I | 24.2 | 20.4 | | 55.4 | | 1 |
| J | 38.0 | 31.0 | 8.0 | 23.0 | | gel only |
| K | 35 | 32 | 7 | 26 | | 2 |
| L | 40 | 30 | 7 | 23 | | gel only |

EXAMPLE 3

The following glass-ceramic powder composites were made:

| Composite | Filler Type | % | Glass Type | % | Firing Temp. | Density | Dielectric Constant | Diss. Factor % | Frac. St | Leachability (wt. loss) |
|---|---|---|---|---|---|---|---|---|---|---|
| 1. | Al$_2$O$_3$ | 60 | A | 40 | 825–950° | 90–95% | 7.8–8.0 | 0.15 | 40–50 | 2.5% |
| 2. | Al$_2$O$_3$ | 75 | A (sol-gel) | 25 | 900–950° | 90–94% | | | | |
| 3. | Al$_2$O$_3$ forsterite | 45 15 | A | 40 | 850–950° | 90–95% | 7.0–7.5 | 0.15 | 30–40 | 0.2 |
| 4. | Al$_2$O$_3$ Cordierite | 45 10 | A | 45 | 850–950° | 90–95% | | | 35–40 | 0.7 |
| 5. | Al$_2$O$_3$ | 50 | G | 50 | 850–950° | 90–95% | 6.0–7.0 | <0.2 | 35–40 | 0.5 |
| 6. | Cordierite | 55 | G | 45 | 825–950° | 90–95% | 5.6 | <0.2 | | 0.2 |
| 7. | Cordierite Al$_2$O$_3$ | 50 10 | A | 40 | 850–950° | 90–95 | | | | |
| 8. | Quartz | 50 | A | 50 | 900–915° | 90–95 | 4.5–5.0 | <0.2 | | <0.4 |
| 9. | Cordierite | 60 | I (sol-gel) | 40 | 900–940° | 90–95 | 6.2 | <0.3 | 25–30 | |
| 10. | Cordierite | 60 | J (sol-gel) | 40 | 900–940° | 90–95 | 5.95 | <0.3 | 25–30 | <0.1 |
| 11. | Cordierite | 60 | K (sol-gel) | 40 | 890–930° | 90–95 | 5.3 | <0.3 | 25–30 | <0.2 |
| 12. | Cordierite | 60 | L (sol-gel) | 40 | 900–930° | 90–95 | 5.9 | <0.3 | 25–30 | <0.2 |
| 13. | Silica | 40 | A | 60 | 940–970° | 90–95 | | | | |
| 14. | Quartz Alumina | 45 10 | A | 45 | 875–930° | 90–95 | 5.7 | <0.2 | | |
| 15. | Cordierite | 56 | E or F | 44 | 875–940° | 90–95 | 5.7 | <0.3 | 27–30 | <0.2 |
| 16. | Al$_2$O$_3$ | 55 | E | 45 | 850–950° | 90–95 | 7.7 | <0.2 | 35–40 | 0.3 |
| 17. | Al$_2$O$_3$ Cordierite | 40 15 | F | 45 | 850–950° | 90–95 | 7.0–7.3 | <0.2 | 32–37 | <0.2 |
| 18. | Al$_2$O$_3$ Quartz | 40 20 | E | 40 | 875–975° | 90–95 | 6.7–7.0 | <0.2 | 30–36 | <0.2 |
| 19. | Cordierite Quartz | 31 25 | E | 44 | 875–950° | 90–95 | 5.5–5.7 | <0.3 | 25–30 | <0.2 |
| 20. | Mullite Quartz | 40 20 | E | 40 | 850–900° | 92–95 | 6.3 | <0.3 | | |

We claim:

1. A method of producing composite ceramic particles having a relatively low sintering temperature, comprising:
    (a) preparing a reagent solution including glassy compounds consisting essentially of calcium oxide, silicon dioxide, boron oxide, and optionally at least one of magnesium oxide and aluminum oxide;
    (b) mixing into the reagent solution a suspension of ceramic particles selected from the group consisting of alumina, spinel, cordierite, mullite, forsterite, quartz, spodumene, eucryptite, and mixtures thereof, to form a mixture; and
    (c) adding to the mixture of precipitating agent so that the glassy compounds precipitate onto and coat the ceramic particles, forming composite ceramic particles.

2. A method according to claim 1, wherein step (b) includes the step of mixing into the reagent solution a suspension of ceramic particles having a narrow size distribution.

3. A method according to claim 1, wherein step (b) includes the step of mixing into the reagent solution a suspension including alumina particles.

4. A method according to claim 1, wherein step (b) includes the step of mixing into the reagent solution a suspension including cordierite particles.

5. A method according to claim 1, wherein step (b) includes the step of mixing into the reagent solution a suspension including silica particles.

6. A method according to claim 1, wherein step (b) includes the step of mixing into the reagent solution a suspension including crystalline quartz particles.

7. A method according to claim 1, further including:
   (d) calcining the composite ceramic particles.

8. A method according to claim 7, wherein the step of calcining occurs at a temperature ranging from approximately 650°–800° C.

9. A method according to claim 7, wherein the calcined ceramic particles are subsequently milled.

10. The method as defined by claim 1, wherein the preparation of the reagent solution is effective to provide composite ceramic particles having a glassy phase consisting essentially of 20–57 wt. % alkaline earth oxides, of which calcium oxide comprises 50–100% and magnesium oxide comprises 0–50%, 23–40 wt. % silicon dioxide, 25–35 wt. % boron oxide, and 0–10 wt. % aluminum oxide.

11. A method of producing a ceramic substrate sinterable at a relatively low temperature, comprising:
   (a) preparing a reagent solution including glassy compounds consisting essentially of calcium oxide, silicon dioxide, boron oxide, and optionally including at least one of magnesium
   (b) mixing into the reagent solution a suspension of ceramic oxide and aluminum oxide; particles selected form the group consisting of alumina, spinel, cordierite, forsterite, quartz, spodumene, eucryptite, and mixtures thereof, to form a mixture;
   (c) adding to the mixture a precipitating agent so that the glassy compounds precipitate onto and coat the ceramic particles;
   (d) separating the coated particles from the liquid;
   (e) drying the separated coated particles;
   (f) forming the dried coated particles into a green compact; and
   (g) firing the green compact at a relatively low sintering temperature to produce a ceramic substrate.

12. A method according to claim 11, wherein the step of firing occurs at a temperature of less than approximately 1500° C.

13. A method according to claim 12, wherein the step of firing occurs at a temperature of less than approximately 1000°.

14. A method according to claim 11, wherein steps (a)–(g) are conducted in such a way so that the substrate has a thermal expansion coefficient of approximately $0.5$–$6 \times 10^{-6}/°C$.

15. A method according to claim 11, further comprising the step of calcining the coated particles of step (e) prior to forming the coated particles into a green compact.

16. A method according to claim 15, further comprising the step of milling the calcined particles prior to forming them into a green compact.

17. A method according to claim 11, wherein step (b) includes the step of mixing into the reagent solution a suspension of ceramic particles having a narrow size distribution.

18. A method according to claim 11, wherein step (b) includes the step of mixing into the reagent solution a suspension including alumina particles.

19. A method according to claim 11, wherein step (b) includes the step of mixing into the reagent solution a suspension including cordierite particles.

20. A method according to claim 11, wherein step (b) includes the step of mixing into the reagent solution a suspension including silica particles.

21. A method according to claim 11, wherein step (b) includes the step of mixing into the reagent solution a suspension including crystalline quartz particles.

22. The method as defined by claim 11, wherein the preparation of the reagent solution is effective to provide glassy compounds consisting essentially of 20–57 wt. % alkaline earth oxides, of which calcium oxide comprises 50–100% and magnesium oxide comprises 0–50%, 23–40 wt. % silicon dioxide, 25–35 wt. % boron oxide, and 0–10 wt. % aluminum oxide.

* * * * *